United States Patent [19]
Kondo

[11] Patent Number: 5,894,454
[45] Date of Patent: Apr. 13, 1999

[54] PORTABLE APPARATUS

[75] Inventor: Yutaka Kondo, Suwa, Japan

[73] Assignee: Seiko Epson Corporation, Tokyo, Japan

[21] Appl. No.: 08/884,174

[22] Filed: Jun. 27, 1997

Related U.S. Application Data

[62] Division of application No. 08/325,960, Oct. 20, 1994, Pat. No. 5,734,625.

[30] Foreign Application Priority Data

Oct. 25, 1993 [JP] Japan ............... 5-266456
Aug. 23, 1994 [JP] Japan ............... 6-198606

[51] Int. Cl.$^6$ .......................... G04B 47/06
[52] U.S. Cl. .......................... 368/11; 368/10
[58] Field of Search .......... 368/10–13, 223–239

[56] References Cited

U.S. PATENT DOCUMENTS

| | | | |
|---|---|---|---|
| 4,287,676 | 9/1981 | Weinhaus | 40/10 R |
| 4,295,472 | 10/1981 | Adams . | |
| 4,312,358 | 1/1982 | Barney . | |
| 4,320,483 | 3/1982 | Vuilleumier | 368/236 |
| 4,407,295 | 10/1983 | Steuer et al. . | |
| 4,450,843 | 5/1984 | Barney et al. . | |
| 4,509,531 | 4/1985 | Ward . | |
| 5,050,612 | 9/1991 | Matsumura . | |
| 5,164,924 | 11/1992 | Saito . | |
| 5,191,891 | 3/1993 | Righter . | |
| 5,375,102 | 12/1994 | Schiavolini | 3687/10 |
| 5,458,140 | 10/1995 | Eppstein et al. . | |

FOREIGN PATENT DOCUMENTS

| | | |
|---|---|---|
| 3040524 | 5/1982 | Germany . |
| 55-100683 | 12/1978 | Japan . |
| 55-010570 | 1/1980 | Japan . |
| 58-142289 | 8/1983 | Japan . |
| 591233 | 9/1977 | Switzerland . |
| 2052051 | 1/1981 | United Kingdom . |
| WO 91/18550 | 12/1991 | WIPO . |

*Primary Examiner*—Bernard Roskoski
*Attorney, Agent, or Firm*—Eric B. Janofsky

[57] ABSTRACT

A portable apparatus is provided which is easy to use, for measuring enviromental and biological data and is useful for health care during exercise. The apparatus includes a measuring unit for measuring biological data, such as, a pulse rate and is disposed on a portion of a side portion of a wrist watch type apparatus body. The measuring unit is pressed by the user with his finger. At least one operation button is provided to operate an electrical circuit for processing the measured biological data.

2 Claims, 9 Drawing Sheets

FIG.−6

PORTABLE APPARATUS

This application is a division of Ser. No. 08/325,960 filed Oct. 10, 1994 U.S. Pat. No. 5,734,625.

BACKGROUND OF THE INVENTION

1. Field of the Invention

The present invention generally relates to a portable apparatus comprising a sensor. More particularly, the present invention is directed to a watch incorporating therein a sensor for measuring biological data, such as the pulse rate, or environment data incorporated in a wrist watch type wrist side measuring device. The present invention also relates to an improved connection mechanism for connecting a wrist watch type apparatus body to an external unit.

2. Description of the Related art

Conventional portable apparatuses of the above-described type are discussed in, for example, U.S. Pat. No. 4,407,295. In a portable apparatus, a sensor for measuring the pulse rate is disposed on a portion of the side area of a wrist watch type apparatus body, while a connector is disposed on a portion of the side surface of the apparatus body which is remotest from the sensor. In this configuration, an external measuring device for measuring the heart beat can be detachably connected thereto. Another example of the conventional portable apparatus, discussed in U.S. Pat. No. 4,450,843 this apparatus, is constructed such that a connector of a sensor for measuring the pulse rate is detachably connected to a side portion of a wrist watch type apparatus body.

However, the above-described conventional portable apparatuses are not easy or convenient to use. Particularly, in recent years, there is a tendency that this type of portable apparatus is used during exercise for health care, and hence there has been an increasing demand for a portable measuring system which is capable of general measurements.

OBJECTS OF THE INVENTION

Accordingly it is an object of the present invention to overcome the problems of conventional portable apparatuses described above.

It is another object to provide a portable apparatus which is easy to use for measuring at least biological and environmental data.

It is a further object of the present invention to provide a portable apparatus which can be used for measuring health related parameters during exercise.

It is additional object of the present invention to provide a portable apparatus which can easily connect with an external unit.

It is yet an object of the present invention to provide a portable apparatus which assures firm connection of a connector of an external unit by means of a magnetic force, and which is capable of preventing adverse influence of the magnetic force on the body of the portable apparatus.

SUMMARY OF THE INVENTION

The portable apparatus according to an aspect of the present invention comprises a measuring unit against which a user presses his or her finger and serves as an biological sensor, the measuring unit being disposed on a portion of a side portion of a wrist watch type apparatus body. At least one operation button is provided for operating electrical circuits for processing the measured data and is provided in the apparatus body. The operation button is disposed on a portion of the side portion different from the portion on which the measuring unit is disposed. More specifically, the operation button includes a button body, and a button guide for movably supporting the button body in a direction in which the button body is operated. The button guide has a support surface which protrudes from an operation surface of the button body.

The portable apparatus according to another aspect of the present invention comprises a wrist side measuring device in which a measuring unit, serving as a biological sensor for measuring biological data, is disposed on a wrist watch type apparatus body. An external measuring device detachably mounted on the wrist side measuring device measures the biological data which is the same as or different from biological data measured by the wrist side measuring device. The wrist side measuring device incorporates an environment data measuring mechanism for measuring environment data, such as, temperature or acceleration of a user's motion. Moreover, the external measuring device is detachably connected to the wrist side measuring device utilizing a magnetic force of a magnet.

The apparatus also comprises a connection structure for connecting either a wrist side apparatus body or a band for securing the apparatus body around an arm to an external unit in which, for example, an external measuring device is incorporated, a connector of either the apparatus body or the band which detachably connects the external unit is provided on a front surface portion of either the apparatus body or the band.

In a structure for detachably connecting an external unit to a wrist side apparatus body or a band utilizing magnets lines of magnetic flux are formed. Additionally, at least two magnets are provided in the external unit, while magnetizable members magnetized by the magnets are provided in either the wrist side apparatus body or the band. Both the magnets and magnetizable members are provided in at least one pair. The magnets and the magnetizable members are connected to each other by a soft magnetic material.

In the present invention, the user can press the measuring unit serving as the biological sensor and the operation button with any two fingers at the same time. Alternatively, when the user is pressing either the measuring unit or the operation button with one finger, the user can press the other button with the other finger at an appropriate time. At that time, since both the measuring unit and the operation button are provided on the side portion of the apparatus body, the user does not have to move his or her fingers awkwardly. More specifically, the user can operate the electrical circuits provided in the apparatus body, e.g., can start and end the operation of, for example, the biological sensor or start and end recording of the data measured by the biological sensor, by pressing the biological sensor with his or her forefinger while supporting the apparatus body with his or her forefinger and thumb and then putting a force in the thumb in that state to push in the operation button. Thus, in this invention, the user can measure the biological data or perform other operations without moving the fingers awkwardly while firmly holding the apparatus body with his or her fingers. Since the user can perform the measurements and the recording of the measured data sequentially, stable measurements are achieved.

In the present invention, the biological data can be continuously obtained while the external measuring device is mounted on the wrist side measuring device. Even if the user does not have the external measuring device, the biological data can be measured by the wrist side measuring device.

Further, since environment data can be measured by the wrist side measuring device, health care can be carried out easily during exercise. This function is very important to the safety of the middle or advanced aged people who participate in physical exercise, like jogging. For example, if the user can be informed of the humidity or the atmospheric temperature in addition to his or her pulse rate or body temperature during exercise, he or she can appreciate the burden given by the exercise. Consequently, an accident which could happen during exercise may be prevented. Furthermore, the acceleration generated by the motion of the user's arm during exercise is detected so as to remove this factor as an influence of the acceleration on the measured pulse rate. By virtue of these features an accurate pulse rate can be obtained.

In the present invention, since the connector for connecting the external unit is provided on the front surface portion of either the wrist side apparatus body or the band, the pressing force the user applies to the apparatus body when he or she mounts the external unit is supported by the user's arm. That is, in a conventional technique in which the connector is provided on the side portion of the apparatus body, when the user mounts the external unit, the apparatus body shifts along the arm. However, such a failure does not occur in this invention, and the user can mount the external unit smoothly. Further, in the present invention, since the connector of the external unit does not protrude from the side of the apparatus body, the back of the user's hand does not touch the protruding portion.

In the present invention, since lines of magnetic flux are formed in at least either the magnets of the connector of the external unit or the magnetizable members of the wrist side apparatus body, a sufficient magnetic force can be obtained and the connector can be firmly connected even when no magnet is provided in the apparatus body. Further, since no magnet is provided in the apparatus body, problems involving attachment of dust, such as iron filing, dust or sand, or erasure of the data on a magnetic card can be prevented.

Other objects and attainments together with a fuller understanding of the invention will become apparent and appreciated by referring to the following description and claims taken in conjunction with the accompanying drawings.

BRIEF DESCRIPTION OF THE DRAWINGS

In the drawings, wherein like numerals represent like parts.

DESCRIPTION OF THE PREFERRED EMBODIMENT

First Embodiment

Figure 1:
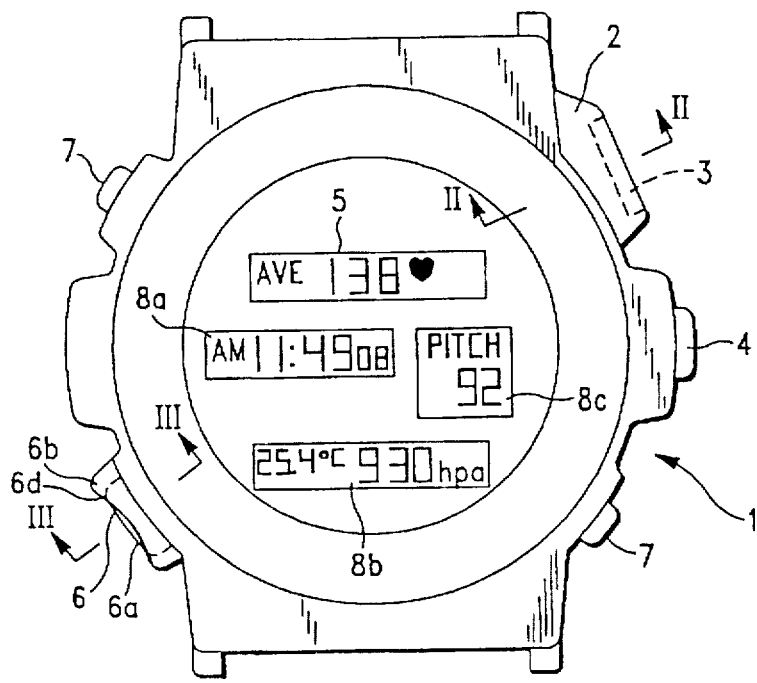
FIG. 1 is a plan view illustrating an embodiment of a portable apparatus according to the present invention.
Figure 2:
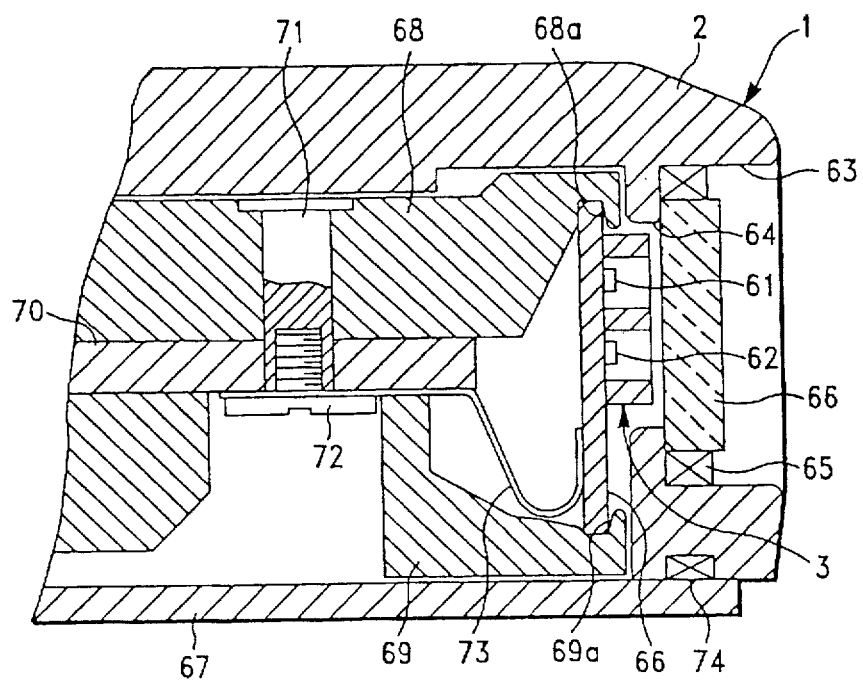
FIG. 2 is a cross-sectional view taken along the line II—II of FIG. 1.

The first embodiment of the present invention will be described below with reference to FIGS. 1 through 5. FIG. 1 is a plan view showing a portable apparatus of the first embodiment. Referring to FIG. 1, reference numeral 1 denotes an apparatus body which has substantially the same shape and size as that of a conventional wrist watch. As such, the apparatus body 1 is secured to an arm using a band (not shown). Apparatus body 1 has a sensor or measuring device 2 such as protruding portion 2 at a side portion thereof. The protruding portion 2 accommodates, for example an infrared radiation sensor 3. The sensor can be a biological type sensor for measuring, for example, pulse rate or body temperature. As shown in FIG. 2, the infrared radiation sensor 3 includes an infrared radiation sensor substrate 60, and a light-emitting element 61 and a light-receiving element (a measuring element) 62 which are arranged on the substrate 60. Protruding portion 2 has an opening 63 at a side surface thereof. Light-emitting element 61 and the receiving element 62 are directed to the outside through opening 63.

An annular shoulder portion 64 is formed in the opening 63 in such a manner that it protrudes inwardly. A glass plate 66 is mounted on the shoulder portion 64 through a gasket 65 to protect the light-emitting element 61 and the light-receiving element 62. A pair of sensor retaining frames 68 and 69 and a main substrate 70 are held between the apparatus body 1 and a rear lid 67. Sensor retaining frames 68 and 69 respectively have grooves 68a and 69a at end portions thereof, and infrared radiation sensor substrate 60 is fitted into these grooves 68a and 69a. Although not shown, various ICs and electric elements are mounted on the infrared radiation sensor substrate 60 and the main substrate 70 and are used in conjunction light-emitting element 61 and light-receiving element 62 to perform the measurement function.

Referring again to FIG. 2, a screwed pin 71 is inserted into the retaining frame 68 and main substrate 70, and a screw 72 is threadedly engaged with an internal screw formed in pin 71, whereby a flexible substrate 73 is mounted between a head portion of screw 72 and main substrate 70. Accordingly, one end of flexible substrate 73 is connected to the main substrate 70. The other end of the flexible substrate 73 is mechanically and electrically connected, by for example soldering, to the infrared radiation sensor substrate 60. Consequently, transmission of electrical signals from the main substrate 70 to the light-emitting element 61 and reception of electrical signals from the light-receiving element 62 to the main substrate 70 are effectuated. Reference numeral 74 denotes a gasket provided between the apparatus body 1 and the rear lid 67.

In the thus-arranged infrared radiation sensor 3, when the operator brings, for example, the bulb of his forefinger into abutment with glass plate 66 while the sensor 3 is energized, the light emitted by light-emitting element 61 is reflected by the forefinger. The reflected light is detected by light-receiving element 62. At that time, maxima and minima values of the reflected light represent the pulsating flow of a blood are measured, thereby enabling measurement of the pulse rate.

Referring back to FIG. 1, reference numeral 4 denotes an operation switch for starting and stopping the measurement by the infrared radiation sensor 3. When switch 4 is depressed, light-emitting element 61 and light-receiving element 62 are turned on or off. Reference numeral 5 denotes a liquid crystal panel for displaying the pulse rate obtained on the basis of the results of the measurement of infrared radiation sensor 3.

Figure 3:
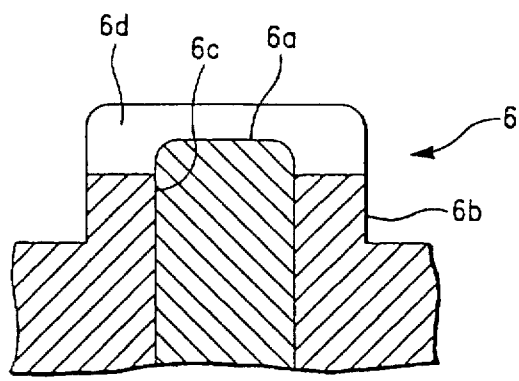
FIG. 3 is a cross-sectional view taken along the line III—III of FIG. 1 of an operational button.

An operation button 6 is mounted on the side portion of apparatus body 1 at a position opposite to that of infrared radiation sensor 3. When the operator depresses operation button 6, the results of the measurement of infrared radiation sensor 3 are stored in a memory incorporated in apparatus body 1. As shown in FIG. 3, operation button 6 preferably includes a button body 6a, and a button guide 6b for slidably supporting button body 6a in a direction in which button body 6a is operated. Button body 6a is accommodated in a through-hole 6c formed in button guide 6b, and is urged in an outward direction by a spring which is not shown. An end surface of button guide 6b preferably has a convex curved surface 6d curved along a direction perpendicular to the surface of FIG. 3. The outermost edge portion of convex curved surface 6d protrudes from an end surface of the button body 6a . The end surface of button body 6a protrudes from the central and innermost portion of convex curved surface 6d.

Further, apparatus body 1 includes a sensor for measuring environmental data such as, the atmospheric temperature, the atmospheric pressure, the humidity, the intensity of ultraviolet radiation, or the wind speed or the frequency (e.g., the stroke of jogging) from the acceleration generated from the movement of the user. Additionally the watch can be provided with a clock or a stop watch. Reference numerals 7 denote switches (operation buttons) for starting and stopping the measurement of the sensor or the like and for selecting the measurement item from the above-mentioned ones. Reference numeral 8a denotes a liquid crystal panel for displaying the time, the elapsed time from the stop watch or other measurement. Reference numeral 8b denotes a liquid crystal panel for displaying the results of the measurement of, for example, the atmospheric temperature or the atmospheric pressure. Reference numeral 8c denotes a liquid crystal panel for displaying the results of the measurement of the pulse rate or the frequency. The measurement results displayed by the liquid crystal panels 8a, 8b and 8c can be varied by depressing the switches 7. As will be appreciated, while only operation button 6 has such structure as that described with respect to FIG. 3, the switch 4 or switches 7 may also have the similar structure.

Figure 5:
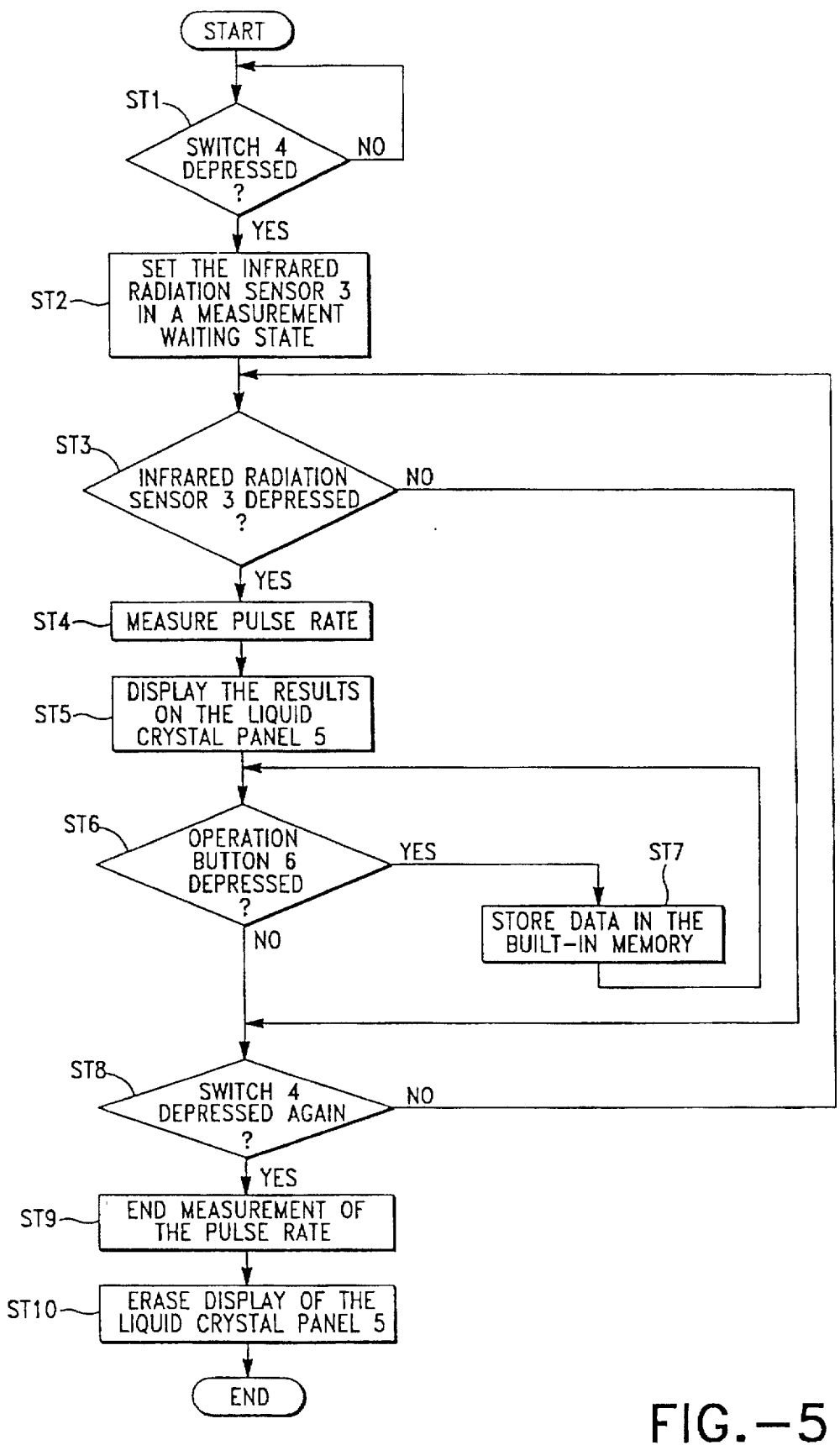
FIG. 5 is a flowchart illustrating the procedures of using the portable apparatus.

The procedures of measuring the pulse rate in the above-described portable apparatus will now be described with reference to FIG. 5. First, the user depresses switch 4 to set infrared radiation sensor 3 in a waiting state in which measurement is enabled (ST1 to ST2). Next, the user grips infrared radiation sensor 3 and operation button 6 with his or her forefinger and thumb, respectively, whereby infrared radiation sensor 3 is depressed and the measurement of the pulse rate of the forefinger is initiated (ST3 to ST4). While infrared radiation sensor 3 is depressed, measurement of the pulse rate continues, and the results of the measurement of the pulse rate is transmitted to and displayed by the liquid crystal panel 5 (ST5). At that time, the user pushes the protruding edge portion of button guide 6b, and does not strongly press the button body 6a.

Next, if the user desires to store the pulse rate in the portable apparatus, he or she slightly slides the thumb sideways or twists it and depresses button body 6a with the bulb of his or her thumb to push down button body 6a against the urging force of the spring (ST6), whereby the results of the measurement of infrared radiation sensor 3 is input in the built-in memory (ST7). Input of the results of the measurement is stopped by releasing the pressing force of button body 6a.

When the user depresses switch 4 again, the measurement of the pulse rate by the infrared radiation sensor 3 is completed, and display of the liquid crystal panel 5 turns off (ST8 to ST10).

To operate the above-described portable apparatus, the user first depresses switch 4 with, for example, his or her forefinger, and then depresses infrared radiation sensor 3 with his or her forefinger. Thereafter, the user depresses operation button 6 strongly at an appropriate time after depression of infrared radiation sensor 3 while still depressing infrared radiation sensor 3 with his or her forefinger. The user continues depressing infrared radiation sensor 3 and operation button 6 simultaneously with his or her forefinger and thumb, respectively. Thereafter, the user depresses switch 4 again. Here, since infrared radiation sensor 3 and operation button 6 are disposed on opposite sides of apparatus body 1, the user can perform series of operations, such as measurement and recording of the pulsed rate, while firmly holding apparatus body 1 with his or her fingers, thus performing stable measurement. Further, since infrared radiation sensor 3, operation button 6 and switches 4 and 7 are provided on the side portion of apparatus body 1, the user can move his or her fingers in a natural motion, enabling operability to be greatly improved.

Figure 4A:
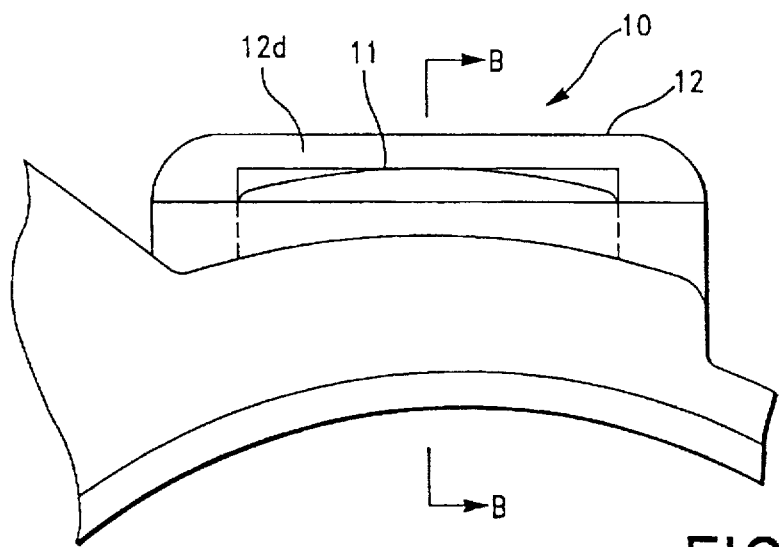
FIG. 4A is a plan view illustrating a modification of the operation button shown in FIG. 1.
Figure 4B:
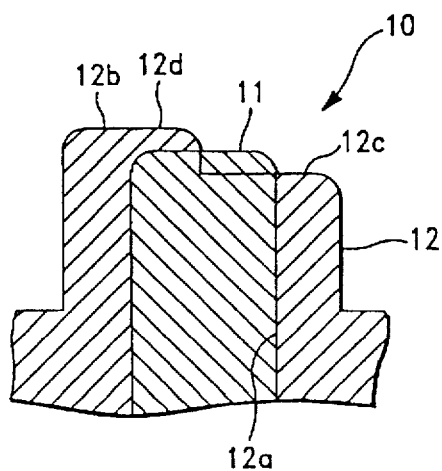
FIG. 4B is a cross-sectional taken along the line B—B of FIG. 4A.

FIG. 4A and 4B show a modification of the operation button in this embodiment. As in the case of the operation button 6, an operation button 10 shown in FIG. 4A includes a button body 11 and a button guide 12. Also referring to FIG. 4B, button guide 12 has a through-hole 12a in which button body 11 is accommodated. An end surface of the button guide 12 has an upper shoulder portion 12b located at a position of the user's thumb nail, and a lower shoulder portion 12c which is lower than the upper shoulder portion 12b. A hanging portion 12d, serving as a stopper of the button body 11, is formed in the upper shoulder portion 12b in such a manner that it hangs halfway over an opening of the through-hole 12a.

In the biological data measuring apparatus having the above-described operation button 10, the user measures the pulse rate while pressing hanging portion 12d of button guide 11 with the bulb of his or her thumb. To record the results of the measurement, the user slightly tilts the thumb and depresses the end surface of 10 button body 11 with the bulb of his or her thumb. In this modification, since button guide 12 has hanging portion 12d, the user can firmly hold infrared radiation sensor 3 and operation button 10. In this arrangement, malfunction of the infrared radiation sensor or the operation button can thus be prevented. As in the case of operation button 6 shown in FIG. 1, switch 4 or 7 may also have the structure of the operation button 10.

Second Embodiment

A second embodiment of the present invention will be described below with reference to FIGS. 6 through 12. The portable apparatus shown in these figures includes a wrist side measuring device 20, and an external measuring device 30 which can be detachably mounted on wrist side measuring device 20. Wrist side measuring device 20 has an infrared radiation sensor 21 for measuring the pulse rate on a front surface thereof, and a switch 22 used to start and stop the measurement by infrared radiation sensor 21 on a side thereof. Reference numeral 23 denotes a liquid crystal panel for displaying the results of the measurement. As shown in FIG. 7, wrist side measuring device 20 has a three-layer internal structure consisting of upper and lower retaining frames 68 and 69 and a main substrate 70 disposed there between. The infrared radiation sensor 21 includes an infrared radiation sensor substrate 60 fixed to upper retaining frame 68, and a light-emitting element 61 and a light-receiving element 62 connected to infrared radiation sensor substrate 60. A glass plate 66 is mounted on the surface wrist side measuring device 20 to protect light-emitting element 61 and light-receiving element 62. Light-emitting element 61 and light-receiving element 62 are electrically connected to the main substrate 70 through coil springs 75.

Retaining frame 68 has an opening 80 in a center thereof and liquid crystal panel 23 is accommodated in opening 80. A glass plate 81 is mounted on the surface of wrist side measuring device 20 to protect liquid crystal panel 23. Various electrical components, such as, ICs 82 and electric elements 83 mounted on the main substrate 70 are accommodated in internal spaces 68b and 69b provided in retaining frames 68 and 69, respectively. In this embodiment, sensors for measuring the atmospheric temperature, the atmospheric pressure, the humidity, the intensity of ultraviolet radiation, the wind speed or the frequency from the acceleration generated by the movement of the user may also be selectively built in the apparatus, as in the case of the first embodiment. The results of the measurement by any of such sensors are displayed by liquid crystal panel 23. In FIG. 7, an acceleration sensor 84 for measuring a stride of the arm of the user who is doing an exercise, such as jogging is shown.

Figure 8:
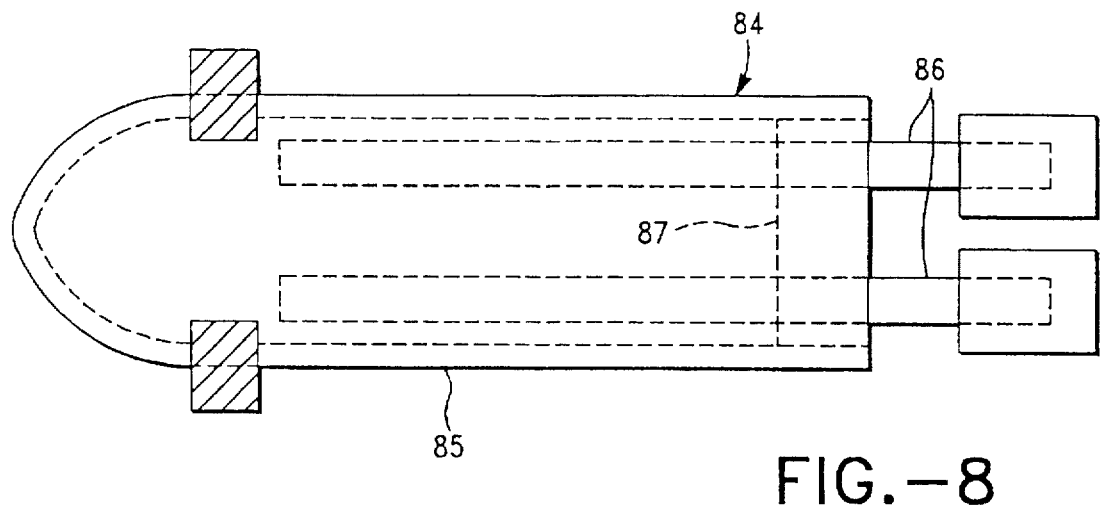
FIG. 8 is a plan view of an acceleration sensor of FIG. 7.

As shown in FIG. 8, acceleration sensor 84 is constructed such that two bar-like terminals 86 fixed to a single piezo-electric element (not shown) are inserted into a quartz tube 85 having a diameter of preferably 2 mm and a length of 8 mm. Reference numeral 87 denotes a lid for closing quartz tube 85 with terminals 86 inserted therein. The two ends of the acceleration sensor 84, i.e., quartz tube 85 and terminals 86, are electrically connect to the main substrate 70 by a soldering process, whereby the piezoelectric element is deformed by an acceleration applied in a direction (which is parallel to substrate 70) perpendicular to the longitudinal direction of the quartz tube 85. Deformation of piezoelectric element is detected by ICs 82 on main substrate 70, and an acceleration value is displayed by liquid crystal panel 23 in response to a detection signal.

Thus, acceleration sensor 84 is disposed such that the direction in which the acceleration is generated, i.e., in which the user swings his or her arm and the longitudinal direction of the quartz tube 85 are perpendicular to each other, as shown in FIG. 7. However, the position at which the acceleration sensor 84 is provided is not limited, if it does not interfere with liquid crystal panel 23, ICs 82 and the electric element 83, and if such arrangement allows terminals 86 to be connected to main substrate 70. The form of the acceleration sensor is not limited to that shown in this embodiment and the acceleration sensor can have any other forms.

In the measurement of the pulse rate of the user who is doing exercise, since the movement of the physical body of the user affects the true pulse rate in the form of noise, the pulse rate measured by the infrared radiation sensor 21 may differ from the true pulse rate. Hence, in this embodiment, the true pulse rate is calculated from the pulse rate obtained by infrared radiation sensor 21 and acceleration detected by acceleration sensor 84 in a circuit on main substrate 70 by the method disclosed in, for example, Japanese Patent Laid-Open No. Sho 60-135029. Infrared radiation sensor 21 measures the pulse rate of the finger of the arm different from that on which wrist side measuring device 20 is mounted. However, the infrared radiation sensor 21 is pressed by the finger during measurement, making the accelerations of the two arms equal to each other. Consequently, it is possible in this embodiment to remove noise generated by the movement of the user's body and thereby display an accurate pulse rate on liquid crystal panel 23.

The acceleration sensor 84 may also be provided in the embodiments shown in FIGS. 1 through 5. In that case, an accurate pulse rate can be obtained by the same method as that employed in this embodiment.

Figure 6:
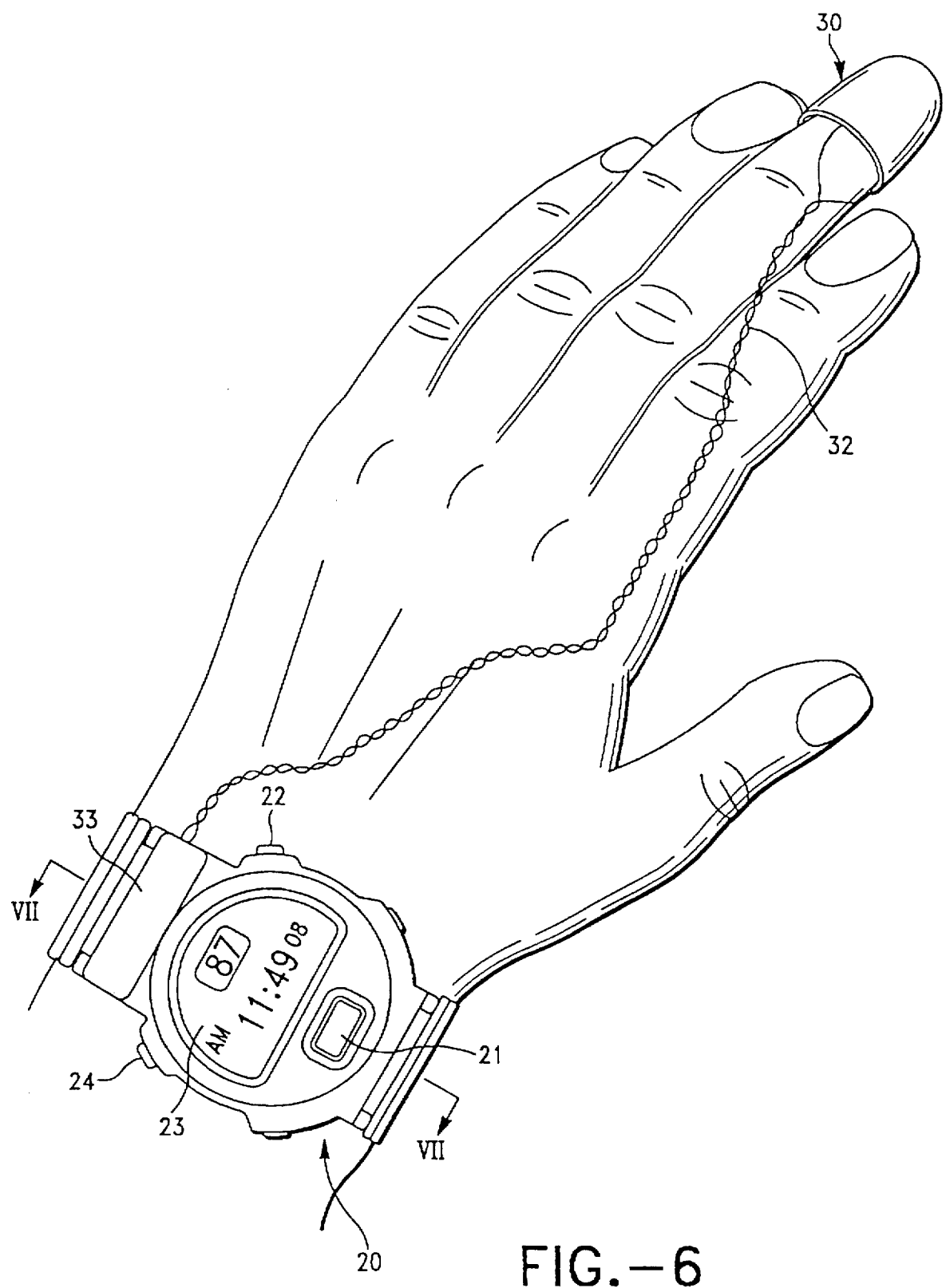
FIG. 6 illustrates another embodiment of the portable apparatus according to the present invention having an external measuring device mounted on a finger.
Figure 7:
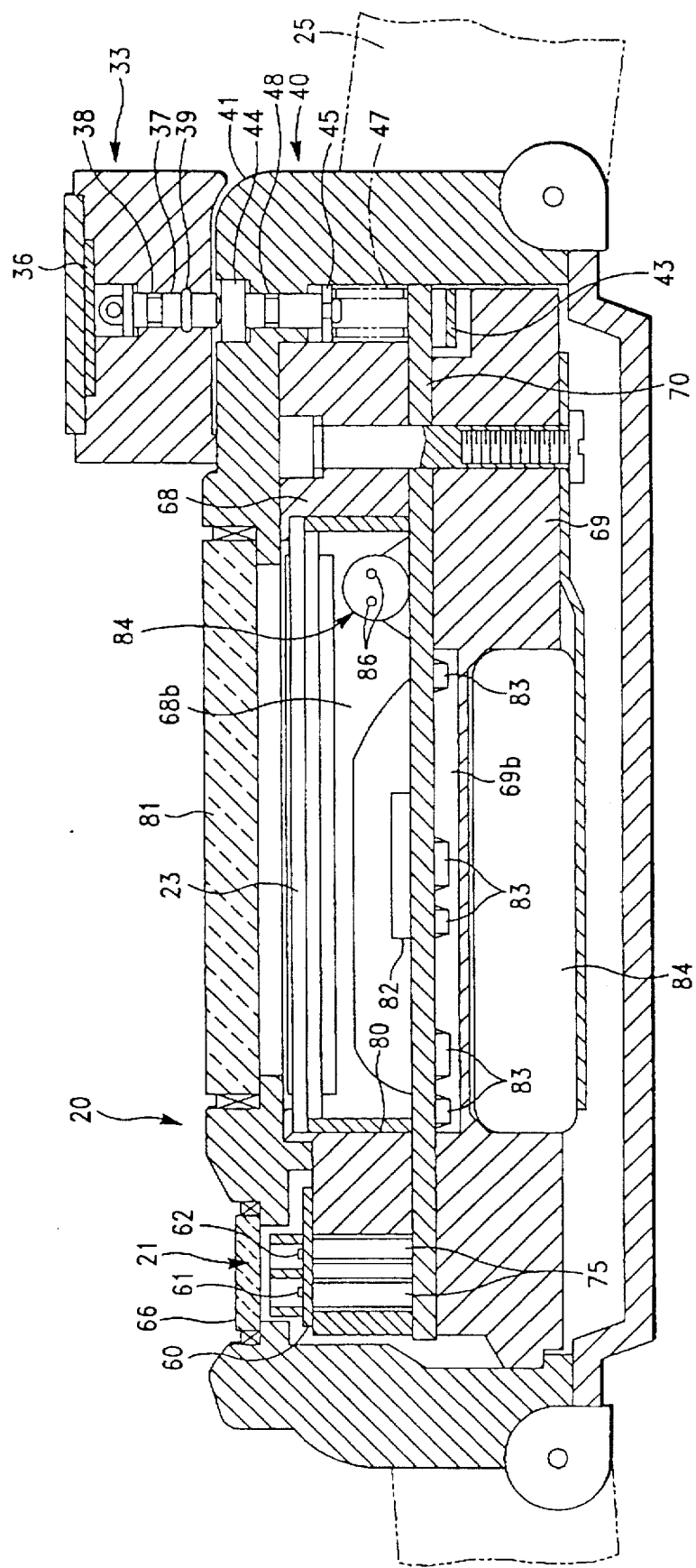
FIG. 7 is a cross-sectional view taken along the line VII—VII of FIG. 6.
Figure 9A:
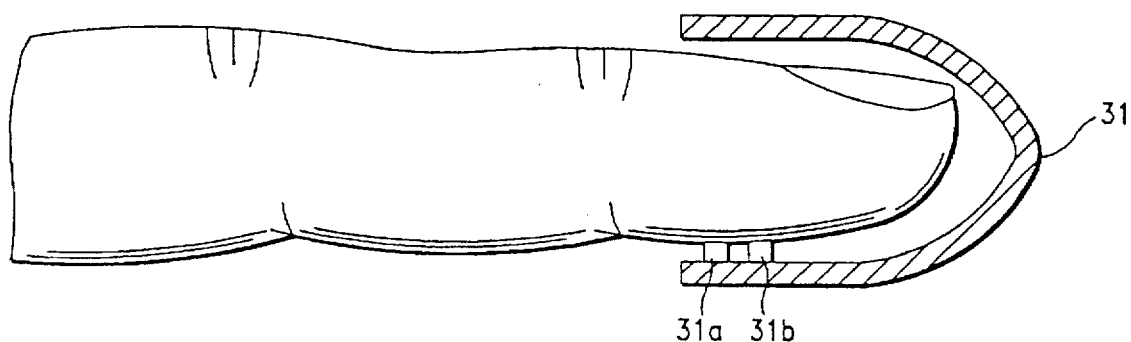
FIG. 9A is a longitudinal cross-sectional view showing an external measuring device mounted on a finger.
Figure 9B:
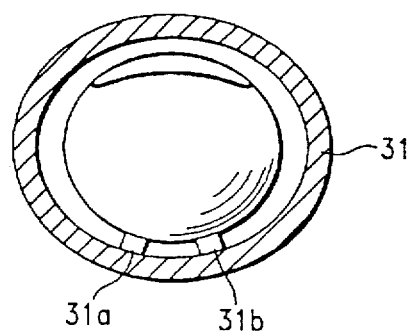
FIG. 9B is a lateral cross-sectional view of FIG. 9A.

As shown in FIG. 9A and 9B, the external measuring device 30 includes a finger stall-like infrared radiation sensor 31 in which a light-emitting element 31a and a light-receiving element 31b protrude inwardly, and a connector 33 connected to infrared radiation sensor 31 via a lead 32 as shown in FIG. 6. External measuring device 30 measures the pulse rate, like the wrist side measuring device 20, and starts or stops measurement when the user depresses a switch 24 disposed on the wrist side measuring device 20. In addition to the infrared radiation sensor for measuring the pulse rate, the external measuring device may also incorporate a sensor for measuring the blood pressure, the body temperature, the heart beat or the like. Further, the form of the external measuring device is not limited to that mounted on the fingertip. The external measuring device may also be formed such that it can be mounted on the root of the finger using a magic tape, may be shaped in a clip-like form so that it can be held on an ear or may be shaped in a glove-like form.

Where external measuring device 30 is designed to measure the pulse rate, the true pulse rate may be calculated in the circuit on the main substrate 70 from both the measured pulse rate and the acceleration detected by the acceleration sensor 84. No acceleration sensor is provided on the finger side, because the acceleration sensor has too big a size to be mounted on the finger, and because there is the possibility that the quartz tube may break when something strikes the acceleration sensor mounted on the finger. Moreover, if an acceleration sensor were to be located on the finger it would detect the fine motion of the finger, thus introducing inaccuracies to such measurements. For the case of measurement of the pulse rate, since an ordinary user may not move the finger very much during exercise, the pulse rate is hardly affected by the acceleration generated by the movement of the finger. It is therefore estimated that an accurate pulse rate can be obtained using the acceleration generated by the stride of the arm.

Figure 11:
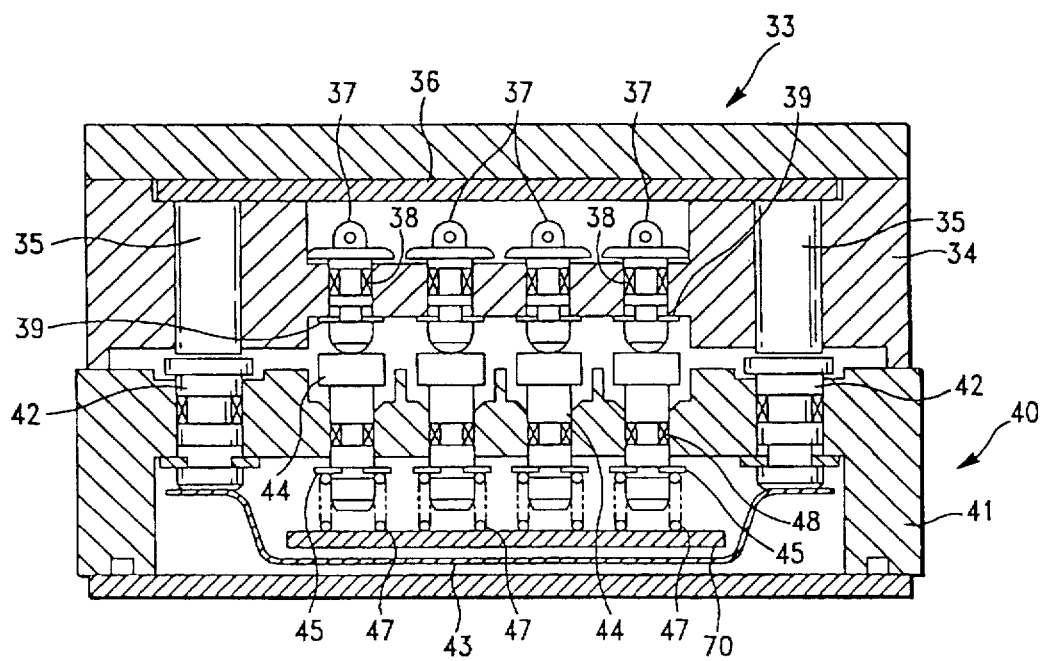
FIG. 11 is a side cross-sectional view showing a connector portion for an external measuring device mounted on a wrist side measuring device.

Referring now to FIG. 11, connector 33 of external measuring device 30 and connector 40 of the wrist side measuring device 20 which receives connector 33 have the following described structures. In a connector body 34, permanent magnets 35 are disposed in such a manner that they are separated from each other. One end of each of the permanent magnets 35 protrudes from an under surface of the connector body 34. The other end surfaces of the permanent magnets 35 are connected with each other by a plate member 36 made of preferably a soft magnetic material. At the central portion of the connector body 34, terminals 37 are mounted in such a manner that axes thereof are directed in the vertical direction. In the figure, reference numeral 38 denotes a water-proof packing material, and reference numeral 39 denotes a washer for securing terminals 37 in connector 33. As will be appreciated by one of ordinary skill in the art where only one pair of magnets has been shown, any number of magnetics may be provided to provide sufficient magnetic force to secure the connector.

Figure 10:
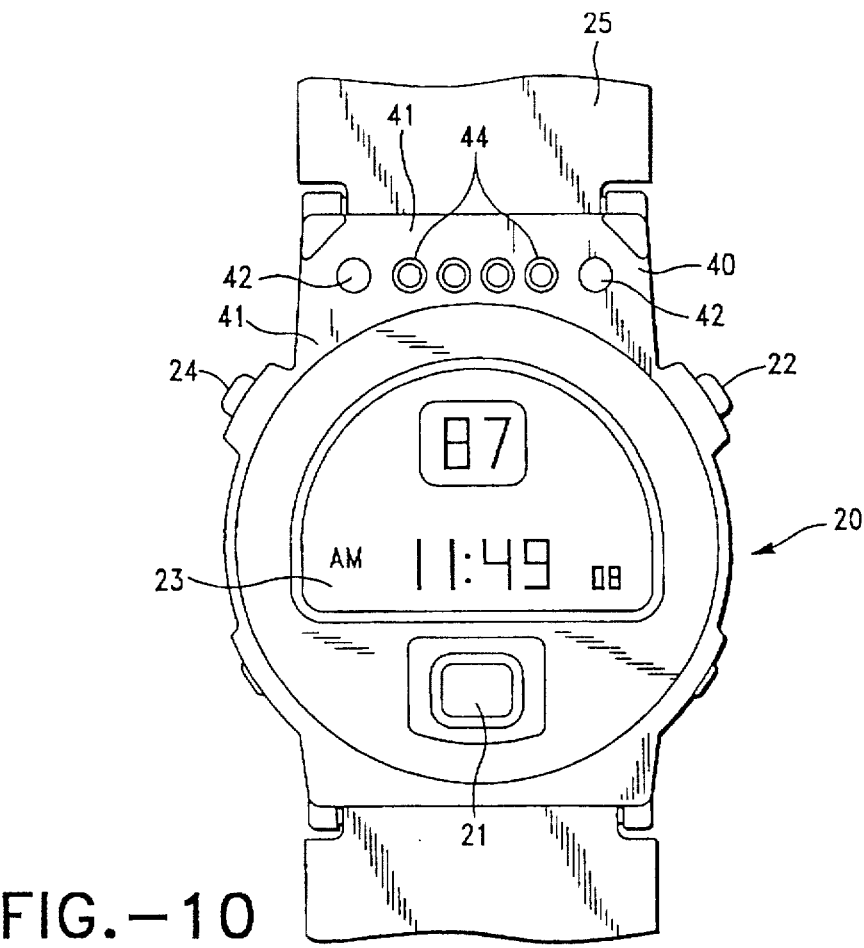
FIG. 10 is a plan view of another example of the portable apparatus.

A connector body 41 of wrist side measuring device 20 has a form which allows it to extend toward a band 25 (see FIG. 10). In connector body 41, magnetizable 15 members 42 preferably made of a soft magnetic material are mounted in such a manner that they face the permanent magnets 35 when the connector 33 is connected to the connector 40. An upper end of each of magnetizable members 42 protrudes from an upper surface of the connector body 41. The lower end surfaces of magnetizable members 42 are connected to each other by a plate member 43 made of a soft magnetic material. At the central portion of connector body 41, terminals 44 are mounted in such a manner that axes thereof are directed in the vertical direction and that they are movable in the vertical direction by a predetermined distance. A washer 45 is mounted on the lower end portion of each of the terminals 44. The connector body 41 also incorporates the portion of main substrate 70 so that a coil spring 47 can be mounted between main substrate 70 and washer 45 to urge terminal 44 in the upward direction. This structure of connector 40 allows terminals 44 to be pressed against the end surfaces of terminals 37 of external measuring device 30 for creating an electrical connection therewith when the connector 33 is connected to the connector 40. Reference numeral 48 denotes a water-proof packing.

In the thus-arranged portable apparatus, it is possible to continuously measure the pulse rate while external measuring device 30 is mounted on wrist side measuring device 20. Even if the user has forgot to take external measuring device 30, it is possible to obtain not only the pulse rate from the wrist side measuring device 20 but also biological data. The measurement of this data can be an important index of the condition of one's health. As noted above this data includes the blood pressure or the body temperature, and environment data, such as the humidity or the atmospheric temperature. Consequently, the above-described portable apparatus enables the user to carry out health care during exercise reliably, thus preventing any accident which would happen during exercise.

As noted above, measurement apparatus 1 can measure the frequency by the stride of the user's arm when the user is, for example, jogging, with acceleration sensor 84. The data obtained by the acceleration sensor 84 can also be used to remove an influence of the acceleration generated by the movement of the user's body from the pulse rate measured by infrared radiation sensor 21 and thereby calculate and display the true pulse rate on liquid crystal panel 23.

Furthermore, in the above-described portable apparatus, when the external measuring device 30 is mounted on the wrist side measuring device 20, lines of magnetic flux result in a magnetic force formed through the permanent magnets 35, the magnetizable members 42 and the plate members 36 and 43. Consequently, a sufficient magnetic force can be obtained even when no magnet is provided on the wrist side measuring device 20, and the connectors 33 and 40 can thus be firmly electrically and mechanically connected to each other. Furthermore, since no magnet is provided in the wrist side measuring device 20, problems involving attachment of dust, such as iron particles are obviated. As a result of this configuration, the erasure of any data on magnetic cards the user may possess can be prevented.

Furthermore, since connector 33 of the external measuring device 30 is constructed so that it is connected to the front surface portion of the wrist side measuring device 20, the pressing force the user applies to wrist side measuring device 20 when he or she mounts the external measuring device 30 is supported by the user's arm, thus enabling smooth mounting of external measuring device 30. Further, since connector 33 of external measuring device 30 does not protrude from the side of the wrist side measuring device 20, an uncomfortable feeling, such as the protruding portion of the connector 33 touching the back of the hand, can be eliminated.

Figure 14:
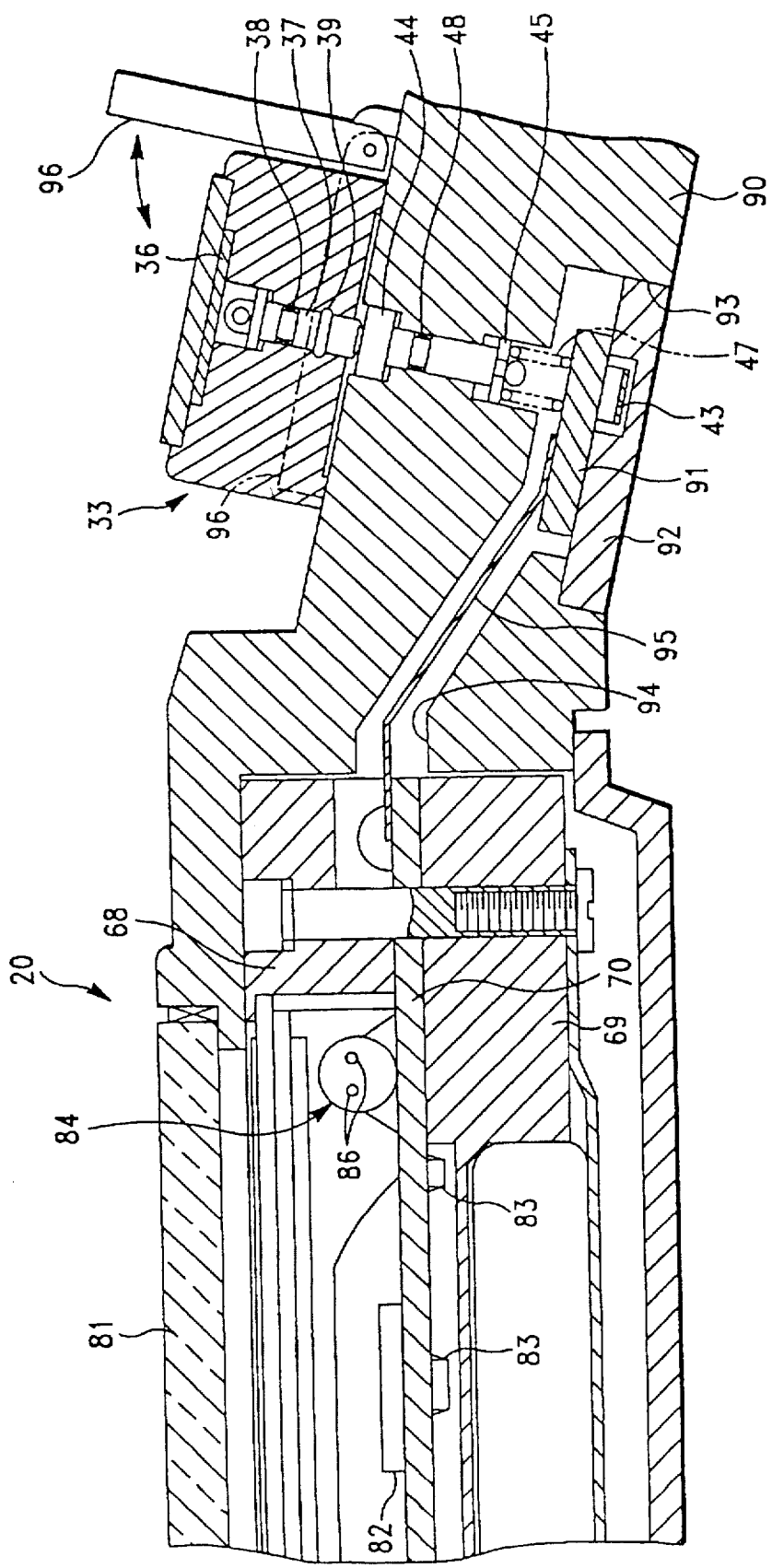
FIG. 14 is a cross-sectional view illustrating another connector portion having an external measuring device mounted on a wrist side measuring device.

FIG. 14 illustrates a modification of connector 40. In FIG. 14, connector 40 is not provided on wrist side measuring device 20 (unlike the case shown in FIG. 7) but provided on the surface of a band 90. Band 90 is formed integrally with wrist side measuring device 20. Connector 40 has the same structure as that described above with the exception that it is supported not by main substrate 70 but by a connector substrate 91. In this modification, the same connector 33 as that described above is used.

A space 92 for accommodating the connector substrate 91 is formed on the rear side of band 90. Connector substrate 91 is disposed in space 92 in a state wherein it is mounted on a mounting plate 92. Also, a cavity 94 for communicating the interior of the wrist side measuring device 20 with space 92 is formed in band 90, and a flexible substrate 95 is inserted into cavity 94 so as to electrically connect the connector substrate 91 to main substrate 70, whereby transmission and reception of electrical signals between main substrate 70 and the connector 40 is enabled. Further, a cover 96 is provided pivotally on the front of the band 90. Cover over 96 is urged toward the band 90 by a spring which is not shown. To connect connectors 33 and 40, cover 96 is raised against the urging force of the spring. When the external measuring device 30 is not used, i.e., when the connectors 33 and 40 are not connected, connector 40 is closed by the cover 96. This arrangement protects connector 40 from potential damage.

In this modification, since the connector 40 is provided on band 90, the size of wrist side measuring device 20 can be further reduced. Accordingly, a gap formed between wrist side measuring device 20 and the user's wrist can be reduced, and consequently, the texture with which the user wears the measuring device 20 can be improved. This feature can prevent the shifting of the measuring device 20 along or about the wrist, caused by the user's movement. Further, since the connector 40 is closed by the cover 96 urged by the spring when the external measuring device 30 is not used, the external appearance of the measuring device 20 is improved while entrance of moisture from outside can be prevented, thus preventing the user's receiving an electric shock causing corrosion of connector 40. Closing of the connector 40 with the cover 96 also enables the connector 40 and hence, the electric parts in the wrist side measuring device to be protected from an externally applied static electricity. The structure of the cover 96 is not limited to the above-described one and cover 96 may also be provided slidably.

Third Embodiment

Figure 12:
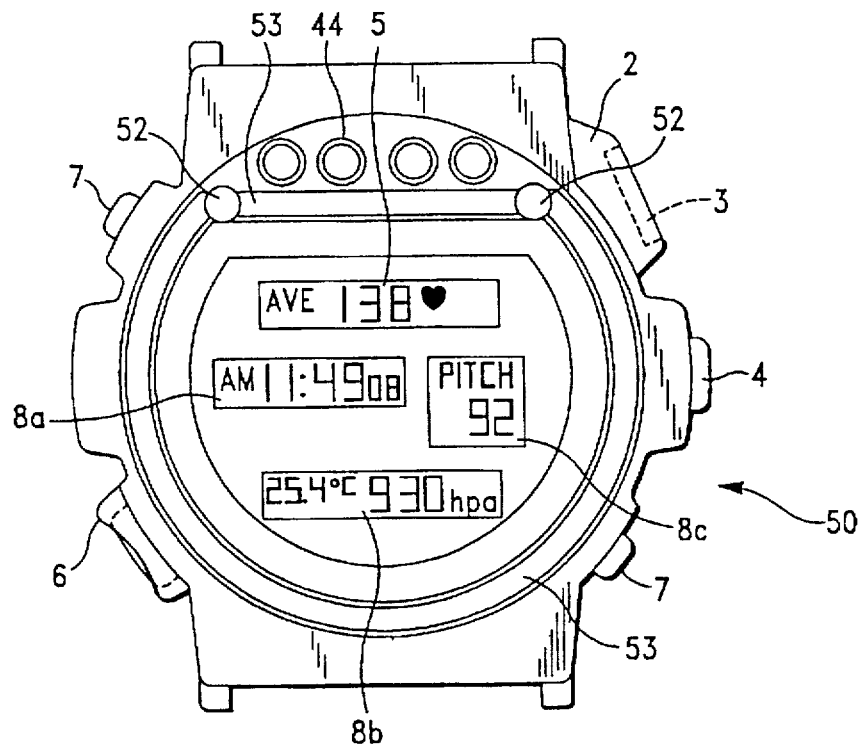
FIG. 12 is a plan view illustrating still another biological data measuring apparatus according to the present invention.
Figure 13:
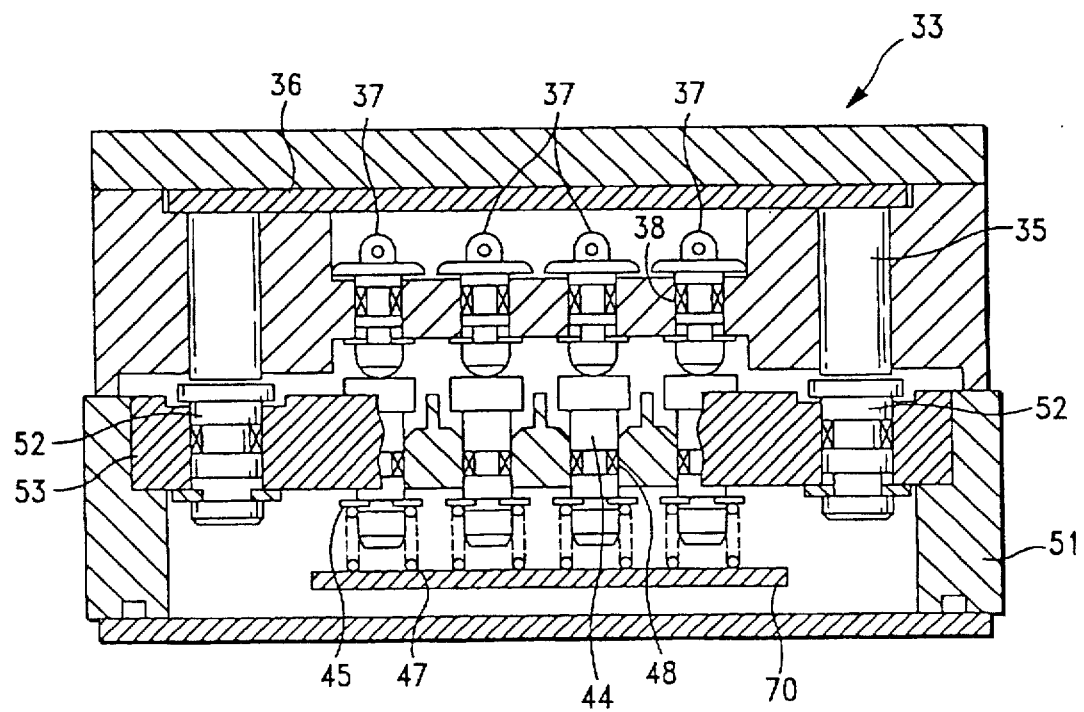
FIG. 13 is a cross-sectional taken along the line VII—VII of FIG. 6 illustrating a modification in which the connector portion shown in FIG. 6 is provided on a front surface of a band.

FIGS. 12 and 13 show still another embodiment of the present invention. The portable apparatus shown in FIGS. 12 and 13 differs from the portable apparatus described above in that magnetizable members of a wrist side measuring device 50 are provided along a peripheral edge portion of a front surface thereof. Reference numerals in these figures identical to those in the other figures represent similar or identical elements, description thereof being omitted.

In a connector body 51, a coupling member 53 for coupling magnetizable members 52 in a straight line and for extending along the peripheral edge portion of the front surface of the wrist side measuring device 50 in an arc form is mounted. The coupling member 53 is preferably made of a soft magnetic material. As a result, when the external measuring device is mounted, lines of magnetic flux are formed which encircle the peripheral edge portion of the front surface of the wrist side measuring device 50. Connector body 51 is provided on the front surface of the wrist side measuring device 50. However, connector body 51 may also be provided on the front surface of the band (not shown), as in the case of the above-described modification.

In the thus-arranged portable apparatus, since the lines of magnetic flux are formed on the front surface portion of either the wrist side measuring device 50 or the band, influence of any electrical noise caused by, for example, static electricity generated by the magnetic force on the electric circuits of wrist side measuring device 50, can be reduced. Further, exposure of coupling member 53 on the front surface of wrist side measuring device 50 can be utilized as a design.

According to present invention, the connection structure for connecting the wrist side apparatus body or the band used to secure the apparatus body around the arm to the external unit in which, for example, the external measuring device is incorporated therein.

As will be understood from the foregoing description, the portable apparatus according to the present invention comprises a measuring unit against which a user presses his or her finger and serving as a biological sensor, the measuring unit being disposed on a portion of a side portion of a wrist watch type apparatus body. At least one operation button for operating electrical components is provided in the apparatus body, the operation button being provided on a portion of the side portion different from the portion on which the measuring unit is disposed. Thus, the user can press the measuring unit serving as the biological sensor and the operation button with any two fingers at the same time, or the user can press either the measuring unit or the operation button with one finger at an appropriate time in a state wherein he or she is pressing the other with the other finger. Since both the measuring unit and the operation button are provided on the side portion of the apparatus body, the user does not have to move his or her fingers awkwardly. Thus, in this invention, since the user can measure the biological data or perform other operations without moving the fingers awkwardly while firmly holding the apparatus body with his or her fingers, stable measurements are achieved.

In the present invention, the biological data can be continuously obtained while the external measuring device is mounted on the wrist side measuring device. Even if the user has left the external measuring device behind, the biological data can be measured by the wrist side measuring device. Further, since environment data and/or biological can be measured by the wrist side measuring device, health care monitoring can be performed easily during exercise.

Furthermore, in the present invention, since the connector for connecting the external unit is provided on the front surface portion of either the wrist side apparatus body or the band, the pressing force the user applies to the apparatus body when he or she mounts the external unit is supported by the user's arm. That is, in a conventional technique in which the connector is provided on the side portion of the apparatus body, when the user mounts the external unit, the apparatus body moves away along the arm. However, such a failure does not occur in the preferred embodiment of the pre-invention, and the user can mount the external unit smoothly. Further, in the present invention, since the connector of the external unit does not protrude from the side of the apparatus body, the back of the user's hand does not uncomfortably touch the protruding portion.

In accordance with another aspect of the present invention, since lines of magnetic flux are formed in at least either the magnets of the connector of the external unit or the magnetizable members of the wrist side apparatus body, a sufficient magnetic force can be obtained and the connector can be firmly connected even when no magnet is provided in the apparatus body. Further, since no magnet is provided in the apparatus body, problems involving attachment of dust, such as iron filings or particles, or erasure of the data on a magnetic card can be prevented.

While the invention has been described in conjunction with several specific embodiments, it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

What is claimed is:

1. A portable apparatus in which an external unit is magnetically and detachably secured to one of a wrist watch type apparatus body and a band, said portable apparatus comprising:

an external unit side connector comprising:
a plurality of magnets for magnetically and detachably securing said external unit to one of said apparatus body and said band wherein said plurality of magnets being separated from each other, and
a first soft magnetic material connecting said plurality of magnets; and
one of said apparatus body and said band comprising:
a plurality of magnetizable members comprising a soft magnetic material wherein said plurality of magnetizable members face said plurality of magnets when said external unit is connected thereto,
a second soft magnetic material connecting said plurality of magnetizable members, wherein when said external unit is connected thereto lines a magnetic flux are formed through said plurality of magnets, said first soft magnetic material, said plurality of magnetizable members and said second soft magnetic material.

2. A portable apparatus in which an external unit is magnetically and detachably secured to one of a wrist watch type apparatus body and a band, said portable apparatus comprising:

an external unit side connector comprising a plurality of magnets for magnetically and detachably securing said external unit to one of said apparatus body and said band, said plurality of magnets being separated from each other, and a first soft magnetic material connecting said plurality of magnets, and one of said apparatus body and said band comprising a plurality of magnetizable members comprising of a soft magnetic material wherein corresponding ones of said plurality of magnetizable members face respective one of said plurality of magnets when said external unit is connected thereto, and a second soft magnetic material connecting said plurality of magnetizable member, wherein when said external unit is connected thereto lines a magnetic flux are formed through said plurality of magnets, said first soft magnetic material, said plurality of magnetizable members and said second soft magnetic material.

* * * * *